United States Patent
Kang et al.

(10) Patent No.: US 9,598,717 B2
(45) Date of Patent: Mar. 21, 2017

(54) ENZYME TREATMENT APPARATUS FOR PROTEINS USING A HOLLOW FIBER MEMBRANE, AND ON-LINE PROTEOMICS METHOD USING SAME

(71) Applicant: KOREA RESEARCH INSTITUTE OF STANDARDS AND SCIENCE, Daejeon (KR)

(72) Inventors: Duk Jin Kang, Daejeon (KR); Sang Ryoul Park, Daejeon (KR); Sook-Kyung Kim, Daejeon (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 0 days.

(21) Appl. No.: 14/345,835

(22) PCT Filed: Sep. 18, 2012

(86) PCT No.: PCT/KR2012/007451
§ 371 (c)(1),
(2) Date: Mar. 19, 2014

(87) PCT Pub. No.: WO2013/042917
PCT Pub. Date: Mar. 28, 2013

(65) Prior Publication Data
US 2014/0302545 A1    Oct. 9, 2014

(30) Foreign Application Priority Data
Sep. 19, 2011  (KR) ........................ 10-2011-0093950

(51) Int. Cl.
| C12Q 1/37 | (2006.01) |
| C07K 1/34 | (2006.01) |
| C12M 1/40 | (2006.01) |
| C12M 1/12 | (2006.01) |
| C12P 21/06 | (2006.01) |
| C07K 1/36 | (2006.01) |
| C07K 1/20 | (2006.01) |

(52) U.S. Cl.
CPC ............... *C12Q 1/37* (2013.01); *C07K 1/20* (2013.01); *C07K 1/34* (2013.01); *C12M 21/18* (2013.01); *C12M 25/12* (2013.01); *C12P 21/06* (2013.01); *C07K 1/36* (2013.01)

(58) Field of Classification Search
None
See application file for complete search history.

(56) References Cited

U.S. PATENT DOCUMENTS

| 4,315,819 A * | 2/1982 | King ...................... B01D 53/22 |
| | | 210/321.8 |
| 4,443,540 A * | 4/1984 | Chervan .................. A23J 3/34 |
| | | 426/46 |
| 2007/0037242 A1* | 2/2007 | Ji ............................ C12P 21/06 |
| | | 435/23 |

FOREIGN PATENT DOCUMENTS

| EP | 1752770 A1 | 2/2007 |
| JP | 2007-044043 A | 2/2007 |
| KR | 10-2007-0001927 A | 1/2007 |
| KR | 10-0792683 B1 | 1/2008 |

OTHER PUBLICATIONS

Aisimo. kiloDalton. Datasheet [online]. Aisimo Corp., Copyright 2009 [retrieved on Sep. 21, 2015]. Retrieved from the Internet: <URL: http://www.aisimo.com/faq/membrane-filter/85.php>, p. 1.*
Luytjes, W. et al. 1987. Primary structure of the glycoprotein E2 of coronavirus MHV-A59 and identification of the trypsin cleavage site. Virology 161: 479-487. specif. p. 479.*
Smiley, K.L. et al. Apr. 1976 Alpha-galactosidase production and use in a hollow-fiber reactor. Applied and Environmental Microbiology 31(4): 615-617., specif. pp. 615, 616.*
International Searching Authority, International Search Report of PCT/KR2012/007451 dated Feb. 21, 2013.
European Patent Office, Communication dated Mar. 26, 2015, issued in corresponding European Application No. 12833157.6.

* cited by examiner

*Primary Examiner* — Renee Claytor
*Assistant Examiner* — Sharon M Papciak
(74) *Attorney, Agent, or Firm* — Sughrue Mion, PLLC

(57) ABSTRACT

Provided are an enzyme treatment apparatus for proteins using a hollow fiber membrane and an on-line proteomics method using same. The enzyme treatment apparatus for proteins according to the present invention can increase a recovery rate of peptides, which are recovered through an enzyme treatment process, by basically solving the problem of low reproducibility of an enzyme activity which may occur during a conventional enzyme treatment process, and can also reduce a time for purification and provide higher yield by performing separation and purification through a single step. In particular, the present invention can be usefully applied for developing a disease-specific protein biomarker through a statistical analysis method having highly efficient detectability for proteins in research for finding biomarkers related to human diseases.

8 Claims, 6 Drawing Sheets

A

B

SEQUENCE LISTING

<160> NUMBER OF SEQ ID NOS: 2

<210> SEQ ID NO 1
<211> LENGTH: 16
<212> TYPE: PRT
<213> ORGANISM: Artificial

```
<220> FEATURE:
<223> OTHER INFORMATION: Synthetic construct

<400> SEQUENCE: 1

Leu Phe Thr Phe His Ala Asp Ile Cys Thr Leu Pro Asp Thr Glu Lys
1               5                   10                  15

<210> SEQ ID NO 2
<211> LENGTH: 25
<212> TYPE: PRT
<213> ORGANISM: Artificial
<220> FEATURE:
<223> OTHER INFORMATION: Synthetic construct
<220> FEATURE:
<221> NAME/KEY: VARIANT
<222> LOCATION: (16)..(16)
<223> OTHER INFORMATION: Any amino acid residues

<400> SEQUENCE: 2

Ser Val Gln Glu Ile Gln Ala Thr Phe Phe Tyr Phe Thr Pro Asn Xaa
1               5                   10                  15

Lys Thr Glu Asp Thr Ile Phe Leu Arg
            20                  25
```

ENZYME TREATMENT APPARATUS FOR PROTEINS USING A HOLLOW FIBER MEMBRANE, AND ON-LINE PROTEOMICS METHOD USING SAME

TECHNICAL FIELD

The present invention relates to an enzyme treatment apparatus for proteins using a hollow fiber membrane, and an on-line proteomics method using the same.

BACKGROUND ART

Recently, research capability has been concentrated on national key scientific technologies from a basic science field up to applied science field. Particularly, various researches into the development of a key original technology associated with diagnosis and treatment of diseases, which is a main interest in bio-medical research fields, have been conducted at home and aboard. In researches into a technology of identifying and finding proteins related to diseases in a novel drug industry field and a bio-life science field, a separating and identifying step of proteins is an essential basic technology and has been importantly used to diagnose, treat, and prevent hard-to-cure diseases such as cancer in the overall research into life science fields. Currently, research into a technology of performing a two-dimensional separation process on each of the protein mixtures using two-dimensional electrophoresis (2DE) or multi-dimensional liquid chromatography analysis of proteins extracted from a normal person and a cancer patient, performing a recovery and enzyme treatment process, and then performing qualitative and quantitative evaluation on two samples using tandem mass spectrometry to thereby find a disease specific protein biomarker has been conducted at home and aboard as a research method through proteomics.

Meanwhile, an enzyme treatment process for various proteins recovered through a multi-dimensional separation process is an essential protein pre-treatment process in a proteomics research field based on a mass spectrometer. In the enzyme treatment process for proteins, after performing a denaturation and alkylation/reduction process on serum, cell lysates, or the like, proteins may be digested into peptides by a reaction process at 37° C. for 12 to 18 using enzymes such as trypsin, LYs-C, or the like. Then, qualitative and quantitative analysis may be performed on the peptides using nanoflow liquid chromatography-electrospray ionization-tandem mass spectrometry (nanoLC-ESI-MS-MS) through a primary separation process of the peptide mixture recovered through the enzyme treatment process according to hydrophobicity of the peptides and a secondary mass spectrometry using a tandem mass spectrometer. A series of enzyme treatment processes for protein as described above may be a most basic and important sample pre-treatment process for proteomic research, but there is a disadvantage in that the enzyme treatment process has a large influence on qualitative and quantitative analysis for standard protein due to complexity and low reproducibility of a conventional enzyme pre-treatment process.

Recently, in order to solve the above-mentioned problem, research for increasing enzyme treatment efficiency by applying various external energy such as an ultrasonic wave, pressure, or the like, in the enzyme treatment process in addition to an on-line enzyme treatment method of using an enzyme-fixed column has been reported.

However, the enzyme treatment method using the enzyme-fixed column and external energy has problems in that additional apparatus configuration is essential and reproducibility of enzyme activity is low due to unbalance of external energy. In addition, there is a limitation in that it is impossible to perform an on-line two-dimensional enzyme treatment for post-translational modifications (PTMs) analysis after translation of various proteins.

DISCLOSURE

Technical Problem

While conducting continuous studies in order to solve the above-mentioned problems, the present inventors found that problems such as low reproducibility and recovery rate generated in a conventional enzyme treatment process may be basically solved by using an enzyme treatment apparatus for proteins using a micro-hollow fiber membrane in order to efficiently analyze a proteome sample and at the same time, more accurate results of qualitative and quantitative analysis for various proteins may be provided using an automated enzyme treatment process, thereby completing the present invention.

An object of the present invention is to provide an enzyme treatment apparatus for proteins using a micro-hollow fiber membrane for efficient analysis of a proteome sample.

Another object of the present invention is to provide an enzyme treatment method using a micro-hollow fiber membrane for efficient analysis of a proteome sample.

Technical Solution

In one general aspect, an enzyme treatment apparatus for proteins using a hollow fiber membrane may include a micro hallow fiber enzyme reactor:

an inlet for receiving proteins-containing sample and enzymes;

a hollow fiber membrane where the proteins are digested by the enzymes; and an outlet for discharging the enzyme reaction products The enzyme treatment apparatus may further include a unit for concentrating and desalting of the enzyme-digested products (e.g., peptides) discharged from the micro hollow fiber enzyme reactor (mHFER), and the enzyme treatment apparatus may further include a separation unit such as mass spectroscopy (MS) according to mass or a degree of hydrophobicity of the peptides.

The hollow fiber membrane may have a molecular weight (M.W.) cutoff value of 10 kDa and a volume of 1 to 10 µl.

In more detail, the hollow fiber membrane of the present invention is to separate protein according to a molecular weight thereof, and any hollow fiber membrane may be used as long as it is used to the above-mentioned purpose. However, it is preferable that a hallow fiber membrane has a molecular weight cutoff value of 10 kDa, an inner diameter of about 200 to 600 µm, an outer diameter of about 500 to 1000 µm, and a volume of 1 to 10 µm and is made of polystyrene sulfonate, poly vinyl chloride, polyacrylonitrile, or a mixture thereof.

The unit for concentrating and desalting of the collected and eluted peptides may be a reverse trapping column, the separation unit according to the degree of hydrophobicity of peptides may be a reverse C18 column, and the separation unit according to the mass of peptides may be an electrospray ionization device.

The enzyme treatment apparatus for proteins may reproducibly and highly efficiently recover peptides by a simple pre-treatment process of digesting protein in the hollow fiber membrane using enzymes, separate peptides by performing nanoflow liquid chromatography-electrospray ionization-tandem mass spectrometry (nanoflow LC-ESI-MS-MS) on the recovered peptides, and compare mass spectrum with protein database to automatically analyze a protein sample.

In other general aspect, an enzyme treatment method for proteins using a hollow fiber membrane may include:

injecting proteins and enzymes into a hollow fiber membrane having a closed distal end opposite to an end to which the proteins and enzymes are injected;

digesting the proteins using the enzyme in the hollow fiber membrane;

collecting resulting enzyme-digested products (e.g., peptides) from the hollow fiber membrane; and eluting and discharging the collected peptides.

The enzyme treatment method for protein may further include concentrating and desalting the collected and eluted peptides and further include separating peptides according to mass or a degree of hydrophobicity thereof.

The protein may be glycoproteins. As a glycoprotein, each of the glycoproteins may be prepared according to various kinds of cell lines, tissue sites in cells, tissues of organ, presence or absence or degrees of drug administration, diet and a nutrition state related to the diet, or presence or absence or progress degree of diseases and be used a sample for diagnosing cancer, but is not limited thereto.

The hollow fiber membrane may have a molecular weight (M.W.) cutoff value of 10 kDa and a volume of 1 to 10 μl.

The concentrating and desalting of the collected and eluted peptides may be performed using a reverse trapping column.

The separating of the peptides according to the degree of hydrophobicity of the peptides may be performed using a reverse non-polar column, more preferably, a reverse C18 column, and the separating of the peptides according to the mass of the peptide may be performed using an electrospray ionization device.

As the enzyme, which is non-specific enzyme, endoproteinase capable of attacking a specific amino acid residue in a protein chain to digest the protein may be used, and one or more selected from a group consisting of trypsin, papain, pepsin, peptide N-glycosidase F (PNGase) may be used as the endoproteinase.

The digesting of the protein using the enzyme may be performed at 30 to 60° C. for 30 minutes to 3 hours through sufficient hydrolysis reactions, and in the case of using the enzyme treatment method for proteins, effects such as reproducibility, accuracy, a decrease in time for analysis, low cost, simplicity, and the like, may be obtained.

Advantageous Effects

The enzyme treatment apparatus for proteins according to the present invention may increase the recovery rate of peptides recovered through the enzyme treatment process, by basically solving the problem of low reproducibility of the enzyme activity which may occur during the conventional enzyme treatment process, and may also decrease the time for purification and provide higher yield by performing separation and purification through a single step.

In addition, the enzyme treatment method for proteins using the apparatus may simply and cheaply break protein into peptides in the enzyme treatment process for protein for a series of proteomics studies. In particularly, the present invention may be usefully applied for developing a disease-specific protein biomarker through a statistical analysis method having highly efficient detectability for proteins in research for finding biomarkers related to human diseases.

(A: Non-glycopeptide, B: glycopeptide)

BEST MODE

Hereinafter, an exemplary embodiment of the present invention will be described in detail with reference to accompanying drawings.

Figure 1:
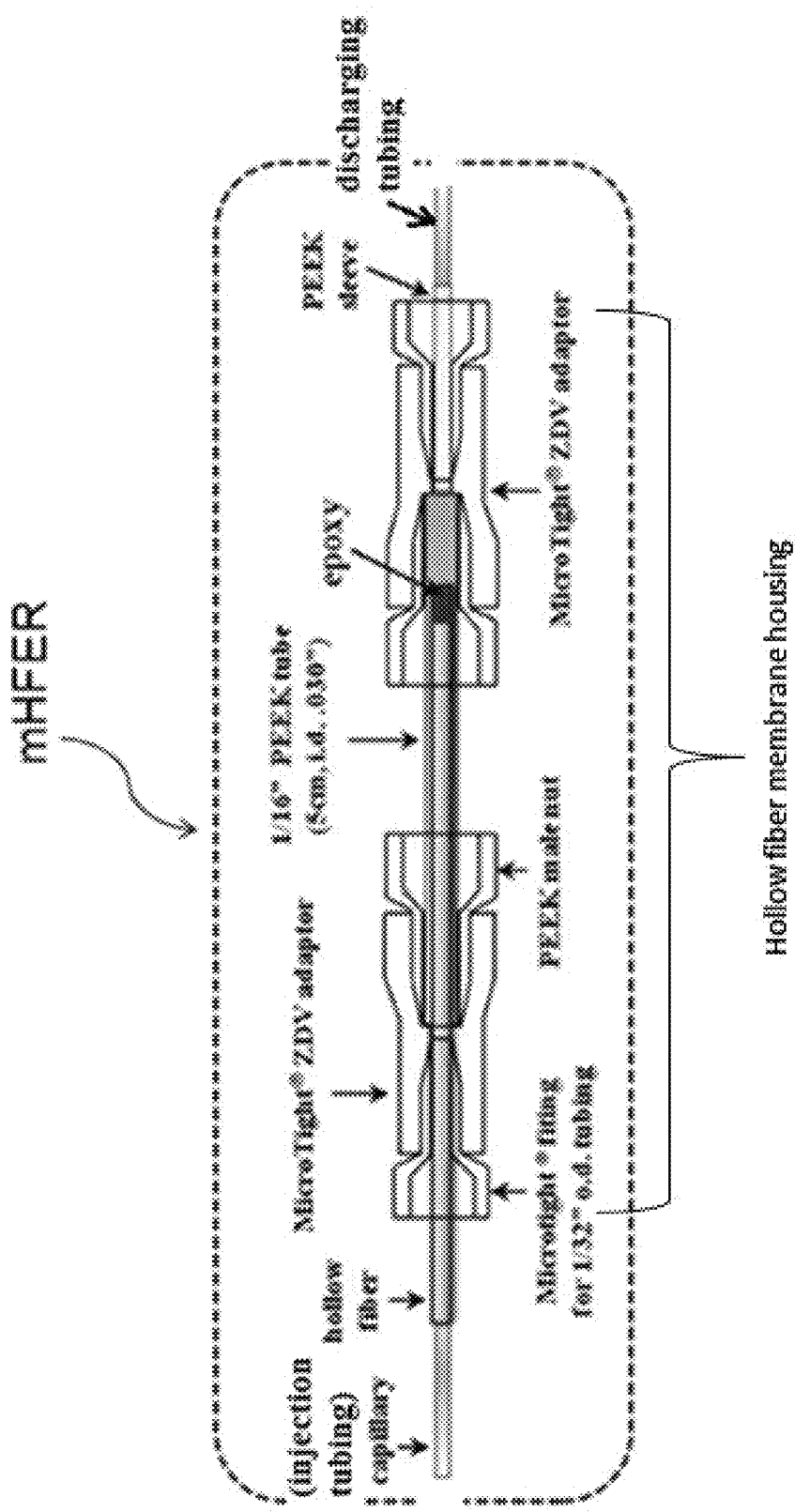
FIG. 1 is a perspective view of a micro hollow fiber enzyme reactor (mHFER), which contains a hollow fiber membrane for an enzyme reaction and a module for coupling the hollow fiber membrane to an inlet part and to an outlet part.

FIG. 1 is a view showing an entire structural feature of an on-line micro-hollow fiber enzymatic reactor, which is an enzyme treatment apparatus using a hollow fiber membrane according to the present invention.

FIG. 1 depicts the illustrative structure of micro hollow fiber enzyme reactor (mHFER). In more detail, a coupling structure of the hollow fiber membrane and injection/discharge tubings is shown in an upper portion of FIG. 1, and the hollow fiber membrane importantly considered in the present invention and a module for the hollow fiber membrane designed for smooth movement of peptides passing through the hollow fiber membrane to the discharge tubing is shown in a lower portion of FIG. 1. The module contains a housing which surrounds the hollow fiber membrane where the enzyme reaction of the peptides occurs and collects peptides that are products of enzyme reaction and move cross the hollow fiber membrane. The housing can be a tubing form and fluid connected to a next unit, such as a concentration/desalting unit (e.g., RP1, RP2 in FIG. 2) of the system. Particularly, in order to enable only the digested products (i.e., peptides) move cross the hollow fiber membrane and flow into the housing, an outlet portion of the hollow fiber membrane is closed by epoxy. A structural feature of the enzyme treatment apparatus is that the inlet of the hollow fiber membrane is open and connected to an inlet of the module, but the outlet of the hollow fiber membrane is not connected but closed.

The module for the hollow fiber membrane in the mHFER comprises a tube housing the hollow fiber membrane, an adaptor, fitting member, and male nut to tightly couple the tube housing the hollow fiber membrane and a fluidic structure (e.g., capillary) connected to other parts of the mHFER system, such as pumps (e.g., micro-pump, binary pump in FIG. 2), a multi-port valve (see, 10-port valve in FIG. 2) to control the operation of nanoflow liquid chromatography-electrospray ionization-tandem mass spectrometry (nLC-ESI-MS/MS). As materials for a housing tube, a 1/16" PEEK (poly ether ether ketone) tubing of a 5 cm length, an inner diameter of 0.030" can be used. For other parts such as fitting parts, Microtight® fitting suitable for 1/32" outer diameter tubing can be used. Also, as shown in FIG. 1, PEEK male nut and sleeves can be used.

Figure 2:
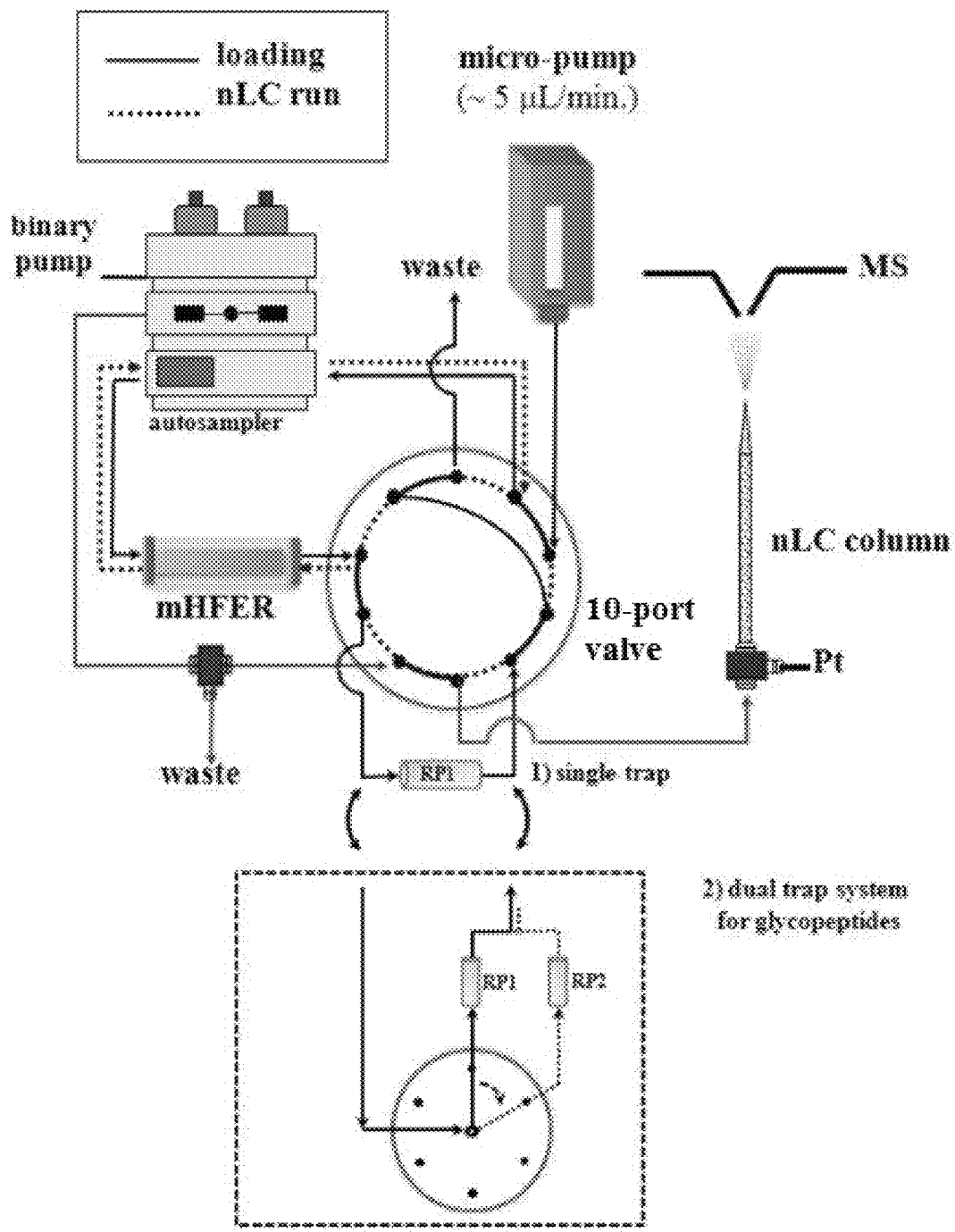
FIG. 2 is a schematic configuration view of an enzyme treatment apparatus for protein according to an exemplary embodiment of the present disclosure, in which the apparatus contains the mHFER shown in FIG. 1.

FIG. 2 shows the entire structure in which the on-line micro-hollow fiber enzymatic reactor (mHFER) corresponding to the enzyme treatment apparatus using a hollow fiber membrane according to the present invention is connected to a shotgun proteomics analyzer for peptide analysis using conventional nanoflow liquid chromatography-electrospray ionization-tandem mass spectrometry (nanoLC-ESI-MS-MS) (shown as a series of nLC column and MS), and this structure may be variously changed according to application fields.

FIG. 2 shows a characteristic structure in which a micro pump capable of being controlled at a flow rate of 10 μl/min or less for movement and injection of protein or enzyme and an sample injector (or autosampler) capable of on-line injecting the protein and enzyme are connected to the on-line micro-hollow fiber enzymatic reactor (mHFER). Particularly, flow paths of all of channels are operated using a 10-port valve for on-line multi-dimensional separation in the present invention, but the flow path may be adjusted suitable for features of an experiment.

The protein and enzyme injected by the micro pump and the sample injector are digested into peptides in the on-line micro-hollow fiber enzymatic reactor, which is the enzyme treatment apparatus using a hollow fiber membrane according to the present invention, and pass through the hollow fiber membrane. Thereafter, the passed peptides move to a reverse trapping column (RP1 and RP2 in FIG. 2) connected to the 10-port valve, such that an on-line concentration and desalting process of the peptides may be performed.

The peptides concentrated in the reverse trapping column are finally separated by a reverse C18 column according to degrees of hydrophobicity of the peptides by changing a channel of the 10-port valve so as to be connected to a flow of the nanoflow binary pump shown in FIG. 2, and then, information on the peptides may be obtained through the tandem mass spectrometer (MS in FIG. 2). However, this configuration may be changed according to application fields.

A recovery method of multi-dimensional peptides formed through a structure standard and enzyme reaction of the on-line micro-hollow fiber enzymatic reactor as the enzyme treatment apparatus using a hollow fiber membrane according to the present invention and a proteomics mass spectrometry for the proteins recovered by the recovered method will be described in detail with reference to FIGS. 1 and 2.

Proteins or glycoproteins and enzymes are injected into a hollow fiber membrane having a volume of about 10 μl shown in FIG. 1 at a flow rate of 5 μl/min by the micro pump and the sample injector. In this case, the collected proteins in the enzymatic reactor need to be easily denatured by using 50 mM ammonium bicarbonate containing 10 mM dithiothreitol (DTT) heated to 37° C. as a solvent. However, a composition and temperature adjustment of a protein denaturation solvent according to the present invention are not limited, and a solvent composition of the existing column heater or capable of denaturizing protein may be used. Particularly, a flow rate of the solvent used to move the protein may be adjusted suitable for a volume and characteristics of the hollow fiber membrane used in the enzymatic reactor.

A structural feature of the on-line micro-hollow fiber enzymatic reactor is that a capillary pipe having an inner diameter of 100 to 200 mm and an outer diameter of 360 mm is used as the injection and discharge tubings used for injection and discharge of the proteins and enzymes in the present invention. However, all kinds of tubings capable of being used in movement of the solvent channel may be used, but it is preferable that a tubing having a small inner diameter is used for smooth movement and recovery of proteins and enzymes.

In order to fix the hollow fiber membrane and the injection tubing shown in FIG. 1, according to the present invention, a capillary pipe having an inner diameter of 200 μm and an outer diameter of 360 μm is injected into the hollow fiber membrane (inner diameter: 400 μm, outer diameter: 800 μm, made of polysulfone and having a size of 6 cm and an end closed using epoxy and then fixed using 1/32-inch fitting (model: F-125) offered from Upchurch Scientific Corp. The fitting can be made of PEEK (poly ether ether ketone). Particularly, in the present invention, an acrylic module self-manufactured so as to be suitable for the outer diameter of the hollow fiber membrane is used in addition to using the 1/32-inch fitting (See the lower portion of FIG. 1), but the module may be manufactured in various shapes so as to be suitable for the composition and flow rate of the used solvent in addition to the inner diameter and the outer diameter of the hollow fiber membrane.

The protein collected through the pump and sample injector is digested into peptides for about 30 minutes by the enzyme injected together with the protein. When molecular weights of the peptides are smaller than a molecular weight cutoff value of the hollow fiber membrane having a molecular weight cutoff value of 10 kDa, the peptides automatically pass cross the hollow fiber membrane and be collected in a housing which surrounds the hollow fiber membrane and fluid connected to a next unit such as reverse trapping column (RP1, RP2 in FIG. 2), where the peptides may be concentrated. In the entire channel tubings used in the present disclosure, a capillary pipe having an inner diameter of 50 mm and an outer diameter of 360 mm is used in all of the connection tubings except for the injection/discharge tubing of the hollow fiber enzymatic reactor, and the connection tubing may be freely used according to mechanical properties.

Figure 3:
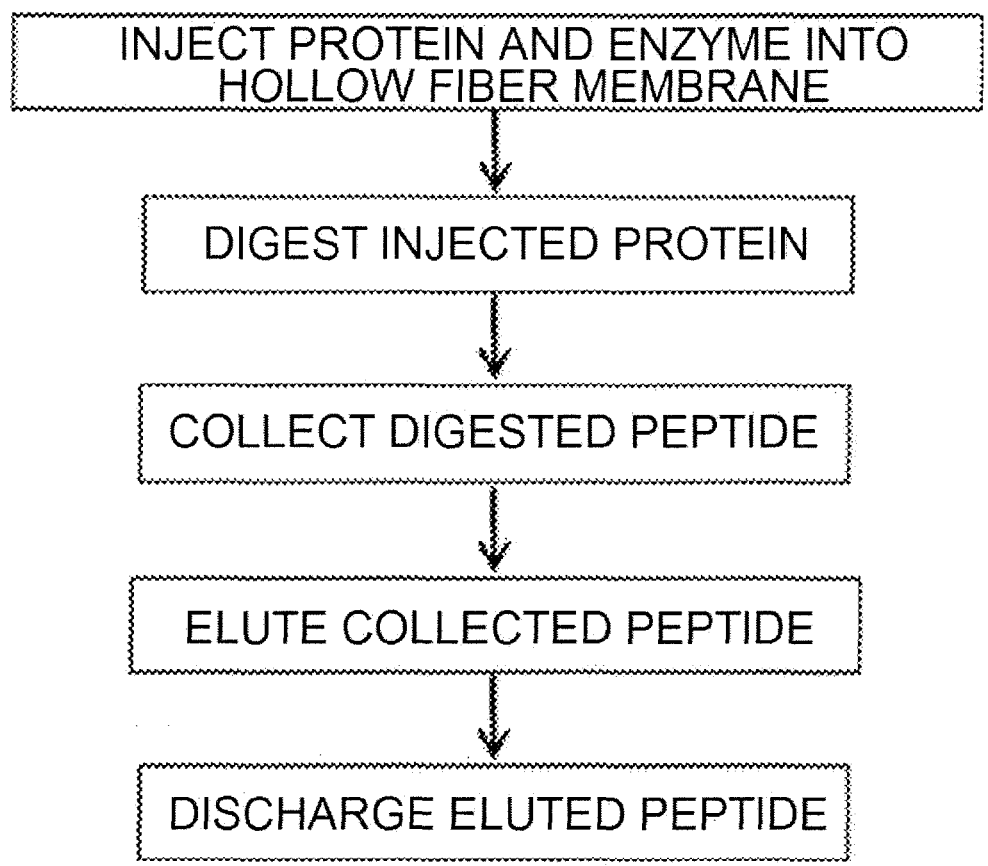
FIG. 3 is a schematic mimetic view of an enzyme treatment method for protein according to the present invention.
Figure 4:
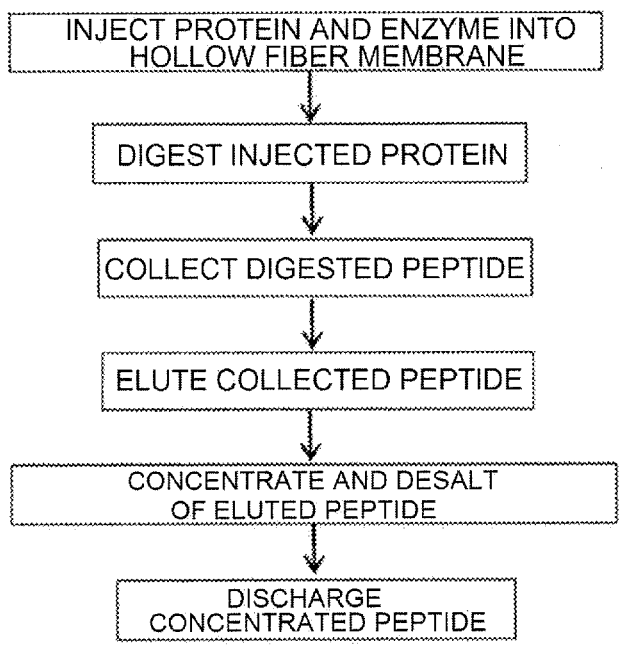
FIG. 4 is a schematic mimetic view of an enzyme treatment method for protein according to an exemplary embodiment of the present disclosure.
Figure 4:
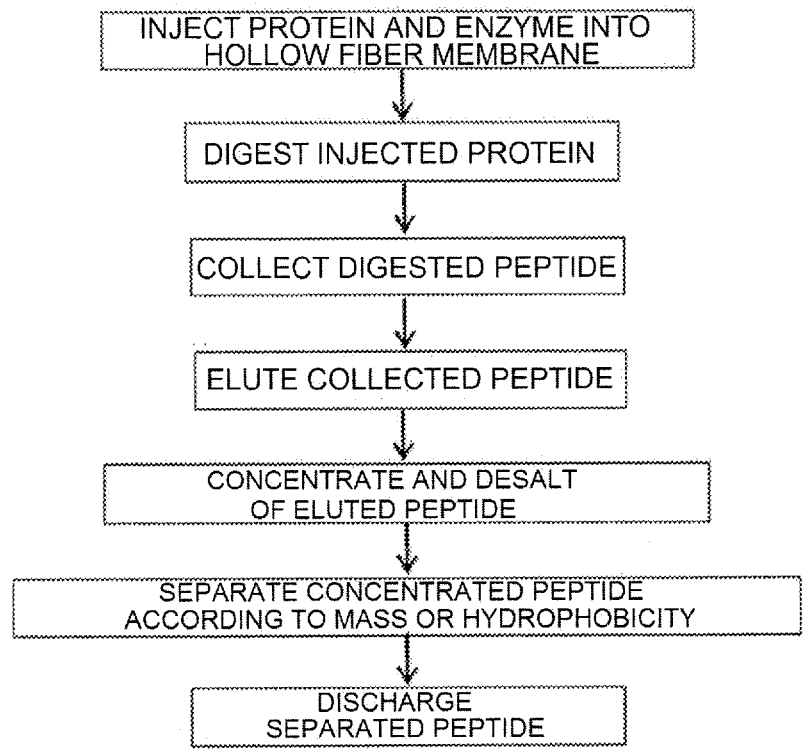
Figure 5:
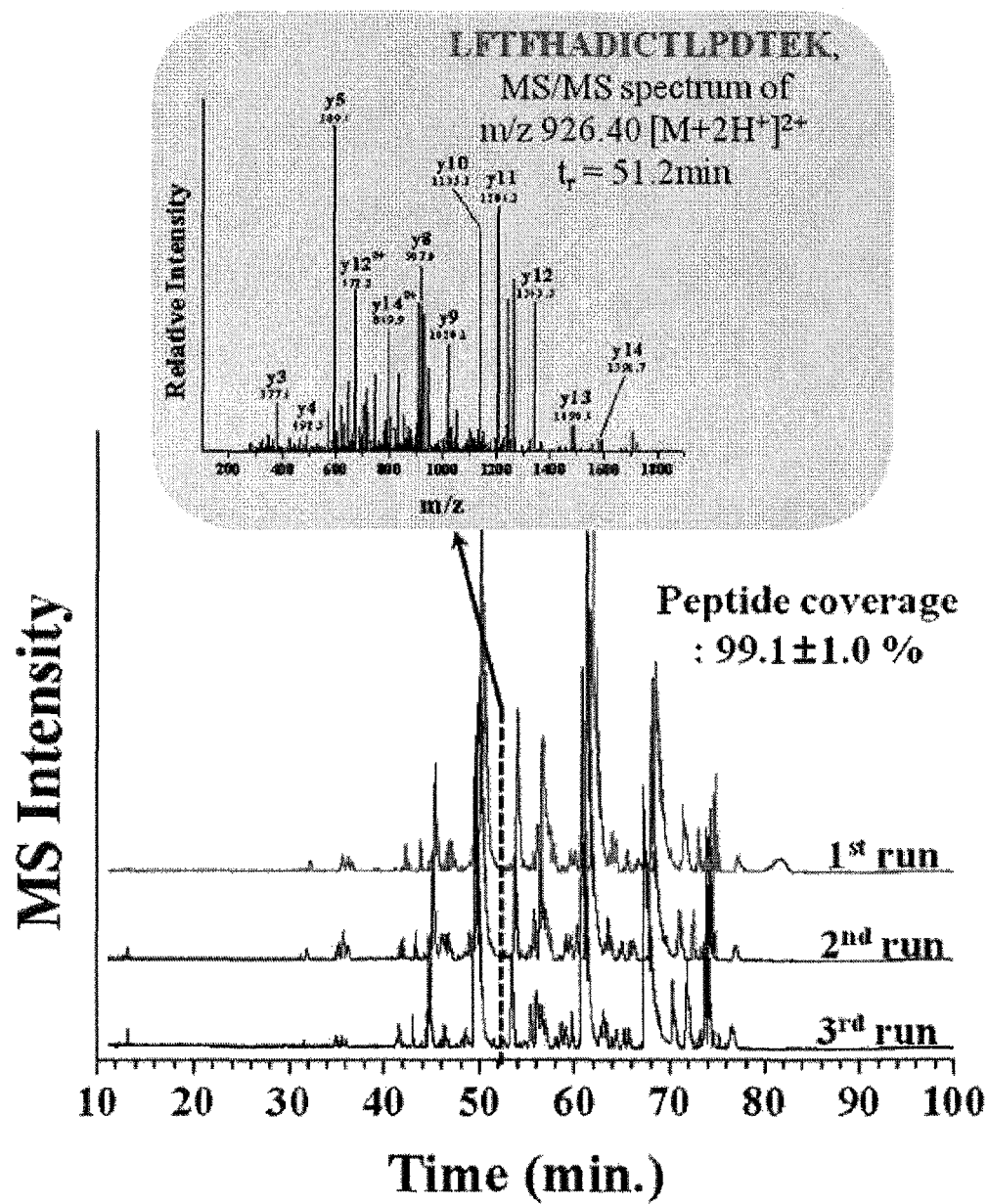
FIG. 5 shows tandem mass spectrometry results for bovine serum albumin (BSA), which is standard protein, using the enzyme treatment apparatus for protein according to the exemplary embodiment of the present invention and MS/MS spectra of LFTFHADICTLPDTEK (SEQ ID NO: 1) (m/z=926.20, [M+2H+]2+) peptide that is detected to be quantitatively low among the tandem mass spectrometry results.

Further referring to FIG. 2, the peptides recovered through the on-line micro-hollow fiber enzymatic reactor are automatically and directly connected to a channel of a nanoLC-ESI-MS-MS apparatus through a channel change of the 10-port valve, and when the peptides are eluted according to the degree of hydrophobicity of the peptides through a nanoLC column filled with C18 according to a reverse solvent gradient, the eluted peptides are introduced into the tandem mass spectrometer through an electrospray ionization process, such that the peptides generated through the enzyme treatment process may be qualitatively and quantitatively analyzed. FIGS. 3, 4, and 5 show processes of the enzyme treatment according to the exemplary embodiments of the application. FIG. 3 shows the basic process containing the enzyme digestion, collecting the digestion product, and eluting it, as described above. FIG. 4 shows the process which additionally contains a step of concentration and desalt of the eluted peptides using, for example, a nanoLC column chromatogrphy" and FIG. 5 shows a process containing another additional step of separation of the concentrated/deslated peptide, using, for example a tandem mass spectrometer.

In addition, a direction of the channel of the on-line micro-hollow fiber enzymatic reactor is automatically changed due to the channel change of the 10-port valve, such that a washing process is performed on the proteins or enzymes used in enzyme treatment during a process of the nanoLC-ESI-MS-MS. Therefore, multi-dimensional enzyme treatment for proteins may be performed.

FIG. 5 shows tandem mass spectrometry results of bovine serum albumin (BSA, 65 kDa) peptides recovered through the on-line micro-hollow fiber enzymatic reactor, which is the enzyme treatment apparatus for protein using a hollow fiber membrane according to the present invention. A base peak chromatogram (BPC) of the nanoLC-ESI-MS-MS obtained by repeatedly performed a trypsin enzyme treatment process on the BSA protein three times is shown in a lower portion of FIG. 5, and MS/MS spectra of LFTFHADICTLPDTEK (SEQ ID NO: 1) (m/z=926.20, [M+2H+]2+) peptide that is detected to be quantitatively low among the tandem mass spectrometry results confirmed in the lower portion of FIG. 5 are shown in an upper portion of FIG. 5.

As shown in FIG. 5, it may be appreciated from analysis results of the BAS peptides generated through the enzyme treatment process of the on-line micro-hollow fiber enzymatic reactor that qualitative and quantitative reproducibility of the generated peptides were significantly high. In addition, as a result of the tandem mass spectrometry of each of the peptide mixtures, it may be confirmed that peptide sequence coverage of BAS was 99.1±1.0%, which shows that qualitative reproducibility due to reproducibility of enzyme treatment may be secured.

In more detail, the upper portion of FIG. 5 shows the MS/MS spectra of LFTFHADICTLPDTEK (SEQ ID NO: 1) (m/z=926.20, [M+2H+]2+) peptide eluted at 52.12 to 52.98 minutes among the peptides confirmed through the each of the nanoLC-ESI-MS-MS, and LFTFHADICTLPDTEK (SEQ ID NO: 1) peptide is represented by a black dotted line in the BPC. As a confirmation result using protein database searching algorithm, all of the probability score values of data obtained from each of the three experiments were 120 or more, which means high reliability. Particularly, reproducible peptide qualitative analysis may be performed on LFTFHADICTLPDTEK (SEQ ID NO: 1) peptide of which a concentration was commonly low in three repetitive analysis using the on-line micro-hollow fiber enzymatic reactor, such that it may be confirmed that the hollow fiber enzymatic reactor has high enzyme treatment efficiency. This result indicates that the hollow fiber enzymatic reactor has high applicability in qualitative-quantitative analysis of peptides generated due to low efficiency of the existing enzyme treatment apparatus for proteins.

Figure 6:
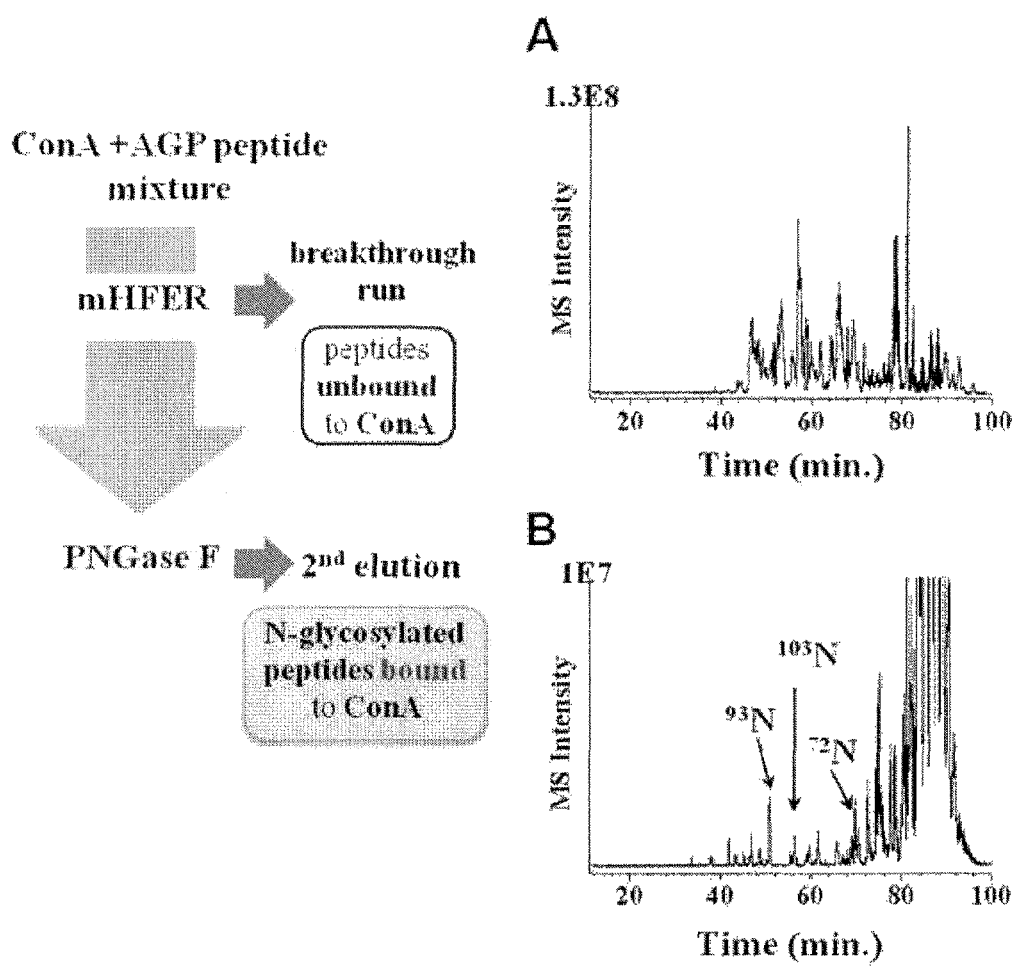
FIG. 6 shows tandem mass spectrometry results for alpha-1-acid glycoprotein (AGP) peptide, which is standard glycoprotein, using the enzyme treatment apparatus for protein according to the exemplary embodiment of the present invention.

FIG. 6 shows nanoLC-ESI-MS-MS results analyzed using alpha-1-acid glycoprotein (AGP), which is standard glycoprotein, as a result of applying the on-line micro-hollow fiber enzymatic reactor, which is the enzyme treatment apparatus for protein using a hollow fiber membrane according to the exemplary embodiment of the present invention, in multi-dimensional on-line glycoproteomics study.

Meanwhile, recently, various researches into glycoprotein as an importance indicator of researches into a technology of fining a biomarker related to human diseases have been conducted at home and aboard. As a biochemical feature of glycoprotein, glycoprotein has a structure in which glycan having various forms is linked to asaparagine N in amino acid sequences. Particularly, in these researches into glycoproteins, research for applying lectin proteins having a selective affinity for a specific glycan among several thousand protein mixtures has been conducted. In the present invention, on-line analysis of glycoprotein is performed using concanavalin A (ConA, 20 kDa) having a selective affinity to high mannose among the lectin proteins.

In more detail, AGP as the standard glycoprotein peptide and ConA were injected to the hollow fiber enzymatic reactor using the micro pump and the sample injector, and as a result, non-glycopeptides that do not have an affinity for ConA lectin protein primarily passed through the hollow fiber membrane to thereby be automatically concentrated in the C18 reverse trapping column, and BPC and tandem mass spectrometry results of peptides collected through the channel change of the 10-port valve obtained by the nanoLC-ESI-MS-MS were shown in an upper portion of FIG. 6.

Further, after tandem mass spectrometry of primary non-glycopeptides, peptide N-glycosidase F (PNGase), which is one of the N-linked endoglycosidases, was injected into the hollow fiber enzyme reactor through the sample injector. Binding sites of glycan and peptides of the N-linked glycopeptides bound to ConA to thereby not pass through the hollow fiber membrane were separated by addition of PNGase F, such that glycopeptides bound to ConA automatically passed through the hollow fiber membrane to thereby be concentrated in the C18 reverse trapping column, and BPC and qualitative analysis results of the peptides obtained by the nanoLC-ESI-MS-MS were shown in a lower portion of FIG. 6.

Qualitative and quantitative differences in BPC between glycopeptides and non-glycopeptides may be easily distinguished from the results shown in FIG. 6. Particularly, among peptides confirmed through PNGase F, a MS/MS spectrum of SVQEIQATFFYFTPN*KTEDTIFLR (SEQ ID NO: 2) (m/z=1449.37, [M+2H+]2+), which is a glycosylation site reported through the existing studies, is shown as Example.

It may be confirmed from the above-mentioned results that the on-line micro-hollow fiber enzymatic reactor according to the present invention significantly contributes to research into glycoprotein. In addition, it may be confirmed that the on-line micro-hollow fiber enzymatic reactor may obtain reproducible result in research for identifying glycoprotein biomarkers related to human diseases.

The invention claimed is:

1. An enzyme treatment method using a hollow fiber membrane, the enzyme treatment method comprising:
   injecting a protein and an enzyme into a hollow fiber membrane, said enzyme being capable of digesting the protein, wherein the hollow fiber membrane has a first end and a second end opposite to the first end and receives the protein and the enzyme through the first end, wherein the second end of the hollow fiber membrane is closed, and wherein the hollow fiber membrane has a molecular weight cutoff value of 10 kDa;
   digesting the protein using the enzyme inside the hollow fiber membrane to produce peptides;
   collecting the peptides from the inside the hollow fiber membrane, said peptides having a molecular weight smaller than the molecular weight cutoff value of the hollow fiber membrane and passing across the hollow fiber membrane; and
   eluting and discharging the collected peptides,
   wherein the protein is a glycoprotein,
   wherein the enzyme is peptide N-glycosidase F, and
   wherein the hollow fiber membrane is housed by a tubing, said tubing surrounding the hollow fiber membrane and collecting the peptides which pass across the hollow fiber membrane.

2. The enzyme treatment method of claim 1, further comprising concentrating and desalting the collected and eluted peptides.

3. The enzyme treatment method of claim 2, further comprising separating the peptides according to mass or a degree of hydrophobicity thereof.

4. The enzyme treatment method of claim 2, wherein the concentrating and desalting of the collected and eluted peptides is performed using a reverse trapping column.

5. The enzyme treatment method of claim 3, wherein the separating of the peptides according to the degree of hydrophobicity of the peptides is performed using a reverse C18 column.

6. The enzyme treatment method of claim 3, wherein the separating of the peptides according to the mass of the peptide is performed using an electrospray ionization device.

7. The enzyme treatment method of claim 1, wherein the hollow fiber membrane has a volume of 1 to 10 μl.

8. The enzyme treatment method of claim 1, wherein the digesting of the protein using the enzyme is performed at 30 to 60° C. for 30 minutes to 3 hours.

* * * * *